US012515020B2

(12) United States Patent
Aranbayev et al.

(10) Patent No.: US 12,515,020 B2
(45) Date of Patent: Jan. 6, 2026

(54) GUIDE-WIRE TORQUE DEVICE

(71) Applicant: Emory University, Atlanta, GA (US)

(72) Inventors: Yuriy Alex Aranbayev, Atlanta, GA (US); William D. Jordan, Jr., Atlanta, GA (US)

(73) Assignee: Emory University, Atlanta, GA (US)

( * ) Notice: Subject to any disclaimer, the term of this patent is extended or adjusted under 35 U.S.C. 154(b) by 812 days.

(21) Appl. No.: 17/787,609

(22) PCT Filed: Dec. 18, 2020

(86) PCT No.: PCT/US2020/066242
§ 371 (c)(1),
(2) Date: Jun. 21, 2022

(87) PCT Pub. No.: WO2021/127585
PCT Pub. Date: Jun. 24, 2021

(65) Prior Publication Data

US 2022/0409867 A1 Dec. 29, 2022

Related U.S. Application Data

(60) Provisional application No. 62/951,630, filed on Dec. 20, 2019.

(51) Int. Cl.
*A61B 5/00* (2006.01)
*A61M 25/09* (2006.01)

(52) U.S. Cl.
CPC ................. *A61M 25/09041* (2013.01); *A61M 2025/09116* (2013.01)

(58) Field of Classification Search
CPC .. A61M 25/09041; A61M 2025/09116; A61M 25/09
See application file for complete search history.

(56) References Cited

U.S. PATENT DOCUMENTS

| | | | | |
|---|---|---|---|---|
| 5,325,746 | A | 7/1994 | Anderson | |
| 5,392,778 | A | 2/1995 | Horzewski | |
| 5,423,331 | A | 6/1995 | Wysham | |
| 5,978,699 | A * | 11/1999 | Fehse | A61M 25/09041 600/585 |

(Continued)

OTHER PUBLICATIONS

International Search Report and Written Opinion for PCT Application No. PCT/US2020/066242 dated Mar. 23, 2021.

*Primary Examiner* — May A Abouelela
(74) *Attorney, Agent, or Firm* — Emory Patent Group

(57) ABSTRACT

A torque device can provide more control of the guidewire with less user effort. The torque device may include a first member, a second member, and a connecting member that couples the first member and the second member; and a locking member slidably coupled to the first member and/or the second member. The locking member may be configured to move along at least a portion of a side of the first member and the second member between one or more positions corresponding to operation states. The operation states may include a closed state in which the side of the first member and of the second member are fixedly secured with respect to the locking member, and one or more open states in which at least a portion of the side of first member and at least a portion of the side of the second member are separated.

18 Claims, 16 Drawing Sheets

(56) References Cited

U.S. PATENT DOCUMENTS

| | | | | |
|---|---|---|---|---|
| 6,190,333 | B1 * | 2/2001 | Valencia | A61M 25/09041 600/585 |
| 6,533,772 | B1 * | 3/2003 | Sherts | A61M 25/0136 279/42 |
| 7,144,378 | B2 * | 12/2006 | Arnott | A61M 25/09041 604/93.01 |
| 7,186,224 | B2 | 3/2007 | Windheuser | |
| 7,690,381 | B2 * | 4/2010 | Bartish, Jr. | A61F 2/4425 128/898 |
| 7,717,865 | B2 | 5/2010 | Boutillette et al. | |
| 7,972,282 | B2 | 7/2011 | Clark et al. | |
| 8,025,629 | B2 | 9/2011 | Shelton | |
| 8,403,869 | B2 | 3/2013 | Kasasbeh | |
| 9,352,130 | B2 * | 5/2016 | Moger | A61M 25/09 |
| 10,076,640 | B2 * | 9/2018 | Nichols | A61M 25/09041 |
| 11,076,924 | B2 * | 8/2021 | Kim | A61B 34/30 |
| 2005/0096566 | A1 * | 5/2005 | Arnott | A61M 25/09041 604/528 |
| 2007/0190856 | A1 | 8/2007 | Hallee et al. | |
| 2010/0191152 | A1 * | 7/2010 | Boutillette | A61M 25/09041 600/585 |
| 2012/0172845 | A1 * | 7/2012 | Kasasbeh | A61M 25/09041 604/528 |
| 2013/0103001 | A1 | 4/2013 | BenMaamer et al. | |
| 2015/0105650 | A1 | 4/2015 | Burkett | |
| 2019/0134357 | A1 * | 5/2019 | Arratia | A61M 25/09041 |
| 2020/0108238 | A1 * | 4/2020 | Matlock | B26D 1/08 |
| 2020/0197682 | A1 * | 6/2020 | Franklin | A61M 25/0097 |
| 2020/0282186 | A1 * | 9/2020 | Blacker | A61M 39/28 |
| 2021/0196412 | A1 * | 7/2021 | Danieli | A61B 34/74 |
| 2021/0345864 | A1 * | 11/2021 | Uihlein | A61B 1/01 |
| 2021/0353910 | A1 * | 11/2021 | Bursavich | A61B 5/15019 |
| 2022/0047344 | A1 * | 2/2022 | Stepanauskas | A61B 34/37 |

* cited by examiner

100

GUIDE-WIRE TORQUE DEVICE

CROSS-REFERENCE TO RELATED APPLICATIONS

This application is the National Stage of International Application No. PCT/US2020/066242 filed Dec. 18, 2020, which claims the benefit of U.S. Provisional Application No. 62/951,630 filed Dec. 20, 2019. The entirety of each of these applications is hereby incorporated by reference for all purposes.

BACKGROUND

Guidewires are used in many interventional procedures such as angiography, balloon angioplasty, chemoembolization delivery of drugs, fallopian tube catheterization, needle biopsy diagnostic tests, uterine artery embolization, etc. Generally, a surgeon uses a torque device to control insertion of a guidewire into a patient and navigation of the guidewire through vessels to reach a lesion or vessel segment in the body. The torque device can allow a surgeon to advance, rotate and grip the wet hydrophilic coating of the guidewire.

Currently available torque devices can require either two hands or another clinician to position, control, remove, as well as otherwise operate. For example, many of the currently available torque devices are loaded from the distal end and can result in unwanted ejection of the guidewire tip from within the patient's body during removal requiring recommencement of the procedure. The currently available devices can therefore increase procedure time, user-error, and risk of harm to patient.

SUMMARY

Thus, there is need for a torque device that provides more control with less user effort, thereby improving the safety and efficiency of interventional procedures that require use of a guidewire.

The disclosure relates to a torque device that can provide more control of the device and/or guidewire with less user effort because the locking mechanism can easily be engaged or disengaged with one finger. The device is also configured to move to a mode when the lock is disengaged but the device remains secured to the guidewire, so there is no risk of the device falling off the guidewire when changing its position on the guidewire.

In some embodiments, the torque device may include a body that includes a first end, a second end, and a length therebetween. In some embodiments, the body may include a first member, a second member, and a connecting member that couples the first member and the second member. The first member and the second member may be configured to move with respect to the connecting member so that the first member and the second member face each other. In some embodiments, the body may include an interior channel disposed along the length and configured to receive a guidewire. In some embodiments, each of the first member and the second member may include a first side and a second side. Each side may be parallel to the length of the body. The connecting member may be disposed on the first side of the first member and the second member.

In some embodiments, the torque device may further include a locking member slidably coupled to the first member and/or the second member. The locking member may be configured to move along at least a portion of the second side of the first member and the second member between one or more positions corresponding to one or more operation states. The one or more operation states may include a closed state in which the second side of the first member and the second side of the second member are fixedly secured with respect to the locking member, and one or more open states in which at least a portion of the second side of first member and at least a portion of the second side of the second member are separated.

In some embodiments, the torque device may include one or more of guiding members disposed on the first member and/or the second member bordering the interior channel. The one or more guiding members may be configured to guide the guidewire into the interior channel.

In some embodiments, the one or more guiding members may include one or more protruding members disposed on one of the first member or the second member and one or more receiving members complimentary to the one or more protruding members. The one or more receiving members may be configured to receive the one or more protruding members and disposed on the other of the first member or the second member.

In some embodiments, the body may include a track disposed on the second side and on which the locking member may be configured to move. Each of (i) the first body portion of the first member and/or (ii) the first body portion and/or the second body portion of the second member may include a rail disposed at least along partially the length thereof that forms the track.

In some embodiments, the first member may include a tip portion and a body portion. The second member may include a tip portion, a first body portion and a second body portion. The first body portion may be between the tip portion and the second body portion.

In some embodiments, the one or more positions may include a first position, a second position and a third position. The third position may be disposed along the length of the body between the first position and the second position. In some embodiments, the first position may correspond to the closed state. The one or more open states may include a first open state and a second open state, and the one or more positions may include a second position and a third position. The second position may correspond to the first open state in which (i) the first body portion of the second member and the first body portion of the first member are separated along the second side and (ii) the second body portion of the second member and the body portion of the first member are separated along the second side. The third position may correspond to the second open state in which (i) the first body portion of the second member and the body portion of the first member are separated along the second side and (ii) the second body portion of the second member and the body portion of the first member abut. The first body portion of the second member and the second body portion of the second member may be separately moveable in (i) the first open state when the locking member is in the second position and/or (ii) the second open state when the locking member is in the third position.

In some embodiments, the tip portion and the body portion of the first member may be integrated. The tip portion and the first body portion of the second member may be integrated.

In some embodiments, the first member and/or the second member may include the interior channel. In some embodiments, the torque device may also include a clamping member disposed along the interior channel of the first member and/or the second member. The clamping member may be configured to clamp on the guidewire when disposed within the interior channel and the body is in a closed state. In some embodiments, the clamping member may be disposed along the first body portion of the first member to oppose the first body portion of the second member.

In some embodiments, the connecting member may be a hinge. In some embodiments, the connecting member may be a living hinge.

In some embodiments, the device may also include a plurality of stopping members disposed along the second side of the first member and/or the second member. The plurality of stopping members may include a first stopping member and a second stopping member. The locking member may be configured to slidably move between the first stopping member and second stopping member. The first position may correspond to when the locking member is adjacent to the first stopping member; and the second position may correspond to when the locking member is adjacent to the second stopping member.

In some embodiments, the plurality of stopping members may be disposed on the second side of the first member and/or the second member.

In some embodiments, the plurality of stopping members may include a third stopping member disposed between the first stopping member and the second stopping member. The first position may correspond to when the locking member is disposed between the first stopping member and the third stopping member. The second position may correspond to when (i) the locking member is disposed between the second stopping member and the third stopping member and (ii) the locking member abuts the second stopping member. The third position may correspond to when (i) the locking member is disposed between the second stopping member and third stopping member and (ii) the locking member abuts the third stopping member.

In some embodiments, the first stopping member may be disposed on the first member and the second member, and the third stopping member may be disposed on the first member and the second member.

In some embodiments, the second stopping member may be disposed on the first member.

In some embodiments, the locking member may include one or more engaging members disposed on a surface. The one or more engaging members may include one or more protrusions and/or depressions.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with reference to the following drawings and description. The components in the figures are not necessarily to scale, emphasis being placed upon illustrating the principles of the disclosure.

DESCRIPTION OF THE EMBODIMENTS

Figure 1:
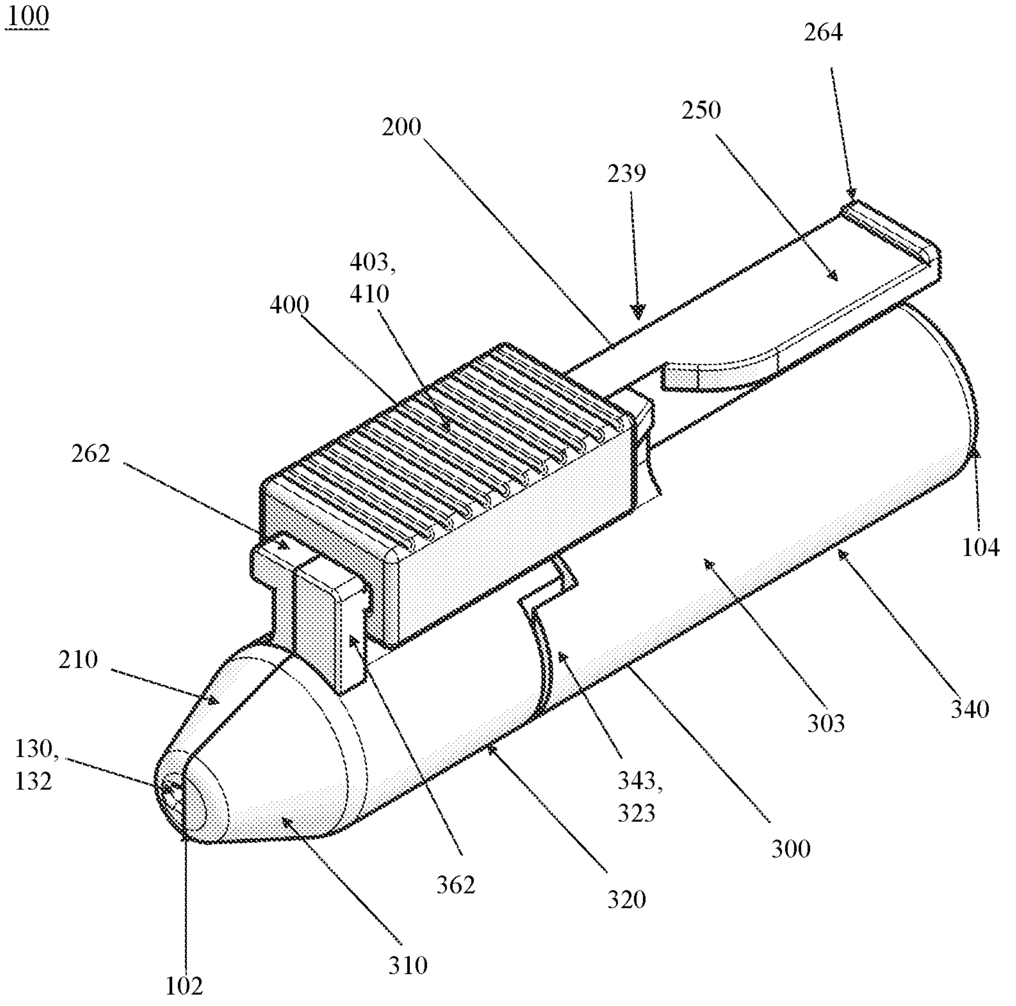
FIG. 1 shows a perspective view of a torque device in a closed state according embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure. Unless otherwise defined herein, scientific and technical terms used in connection with the disclosure shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. As used herein, the term "one or more" such as one or more members of a group of members, can be understood to encompass inter alia a reference to any one of the members, or to any two or more of the members, such as, e.g., any >3, >4, >5, >6 or >7 etc. of the members, and up to all of the members.

The torque device according to the disclosure can provide easy advancement for positioning and maneuvering through a vessel during a procedure using a guidewire. The torque device according to disclosure can allow tightening, advancing, and loosening of the guidewire using only one-hand of the clinician (e.g., surgeon) so that the other hand can be used to secure the positioning of the guidewire within a patient. The torque device can be side-loaded onto the guidewire, thereby enabling easy placement of the torque device at any position along the guidewire (i.e., does not need to be loaded from the distal end of the guidewire). This can prevent unwanted ejection of the guidewire tip from within a patient's body during removal of the device. Additionally, this can prevent vessel dissection from unwanted movement of the guidewire. The torque device according to the disclosure also includes a locking member for opening and closing the torque device into one or more states that can be moved along the length of the device using only one-hand, thereby enabling easy tightening, advancing, and loosening of the guidewire using the torque device. Thus, the torque device according to the disclosure can result in a quicker and safer procedure for both the patient and medical staff.

Figure 2:
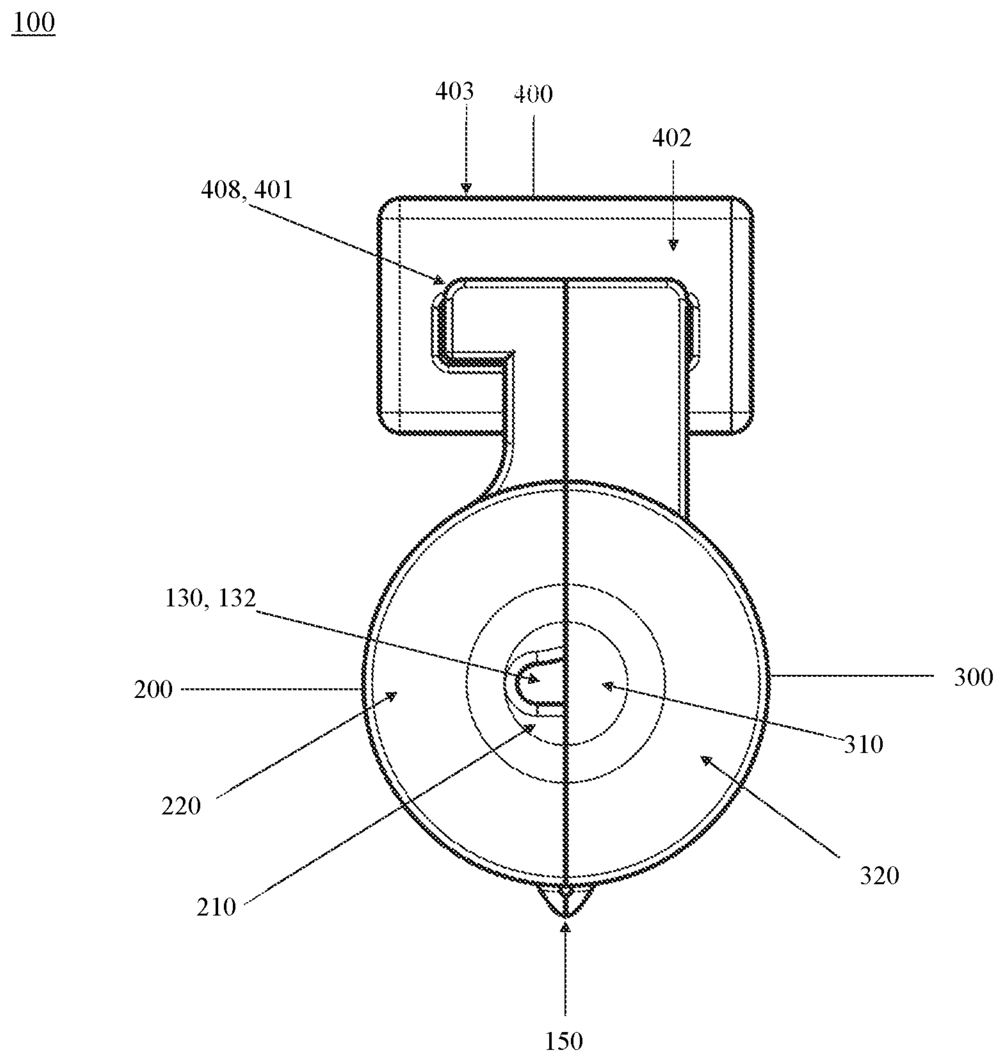
FIG. 2 shows a front view of the torque device shown in FIG. 1.
Figure 3:
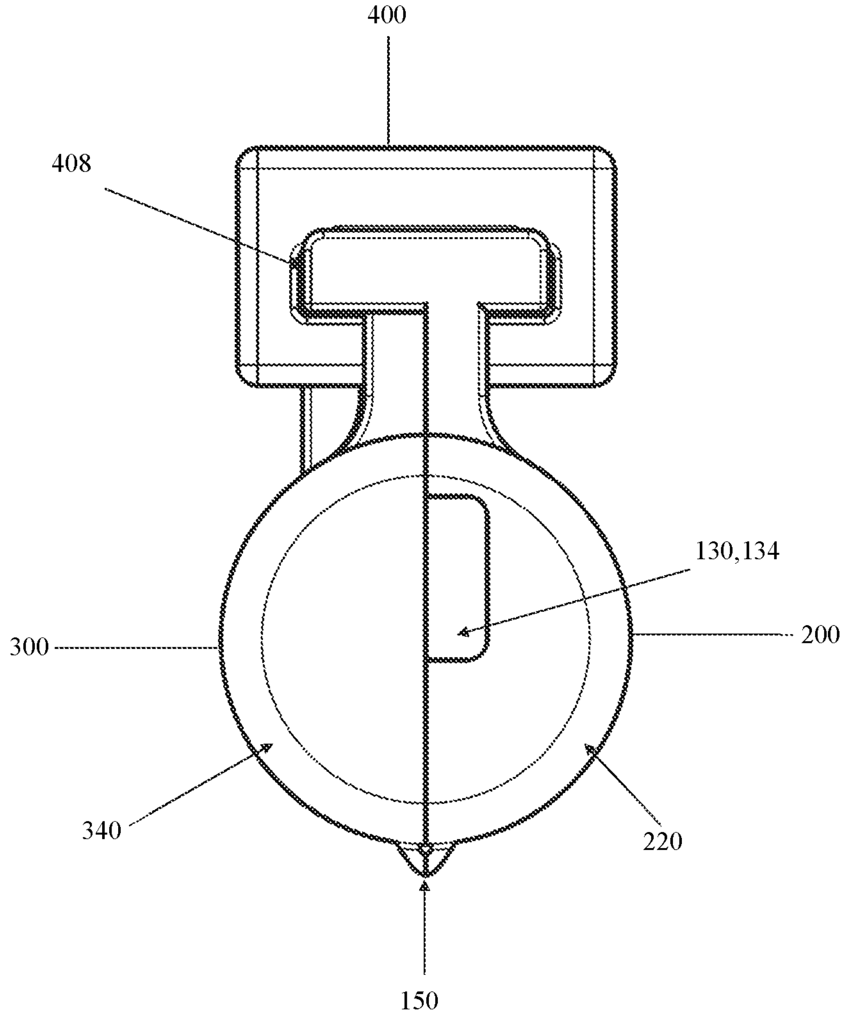
FIG. 3 shows a back view of the torque device shown in FIG. 1.
Figure 4:
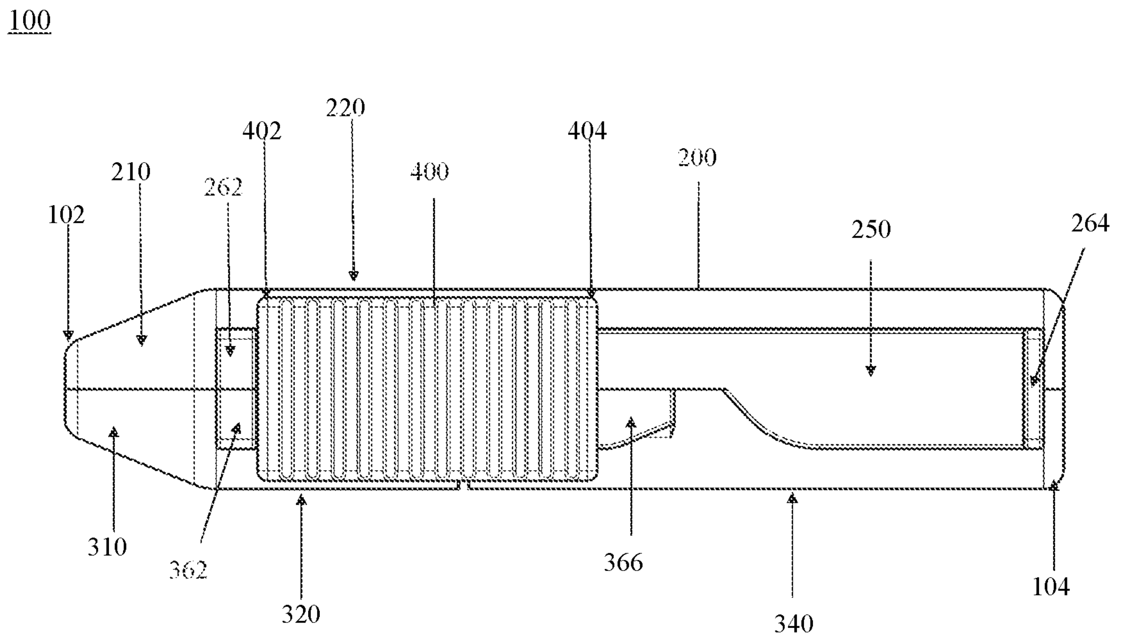
FIG. 4 shows a top view of the torque device shown in FIG. 1.
Figure 5:
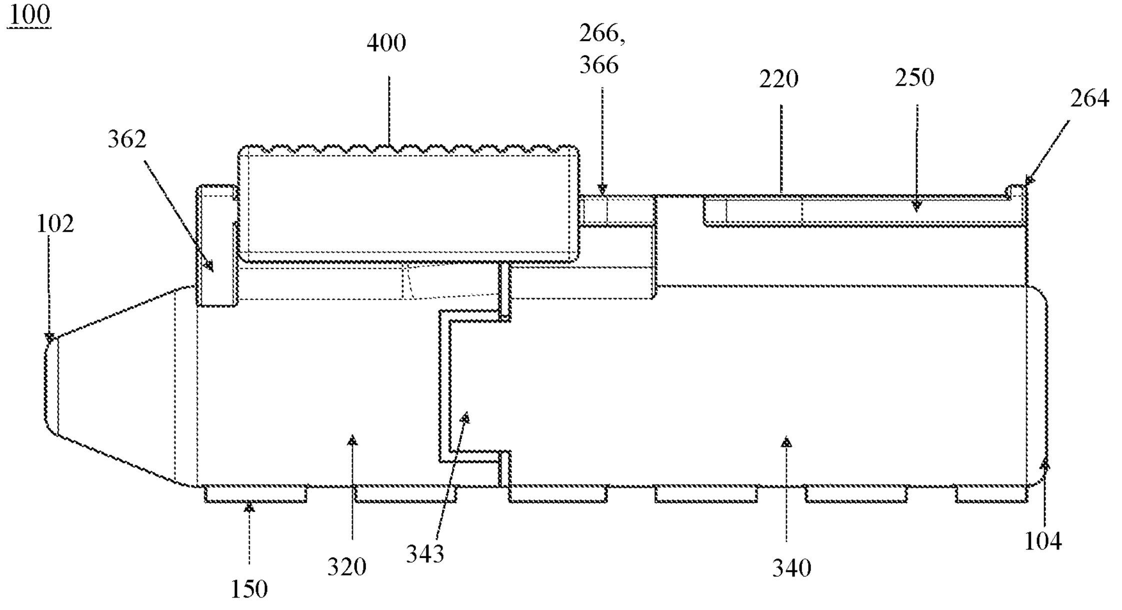
FIG. 5 shows a side view of the torque device shown in FIG. 1.
Figure 6:
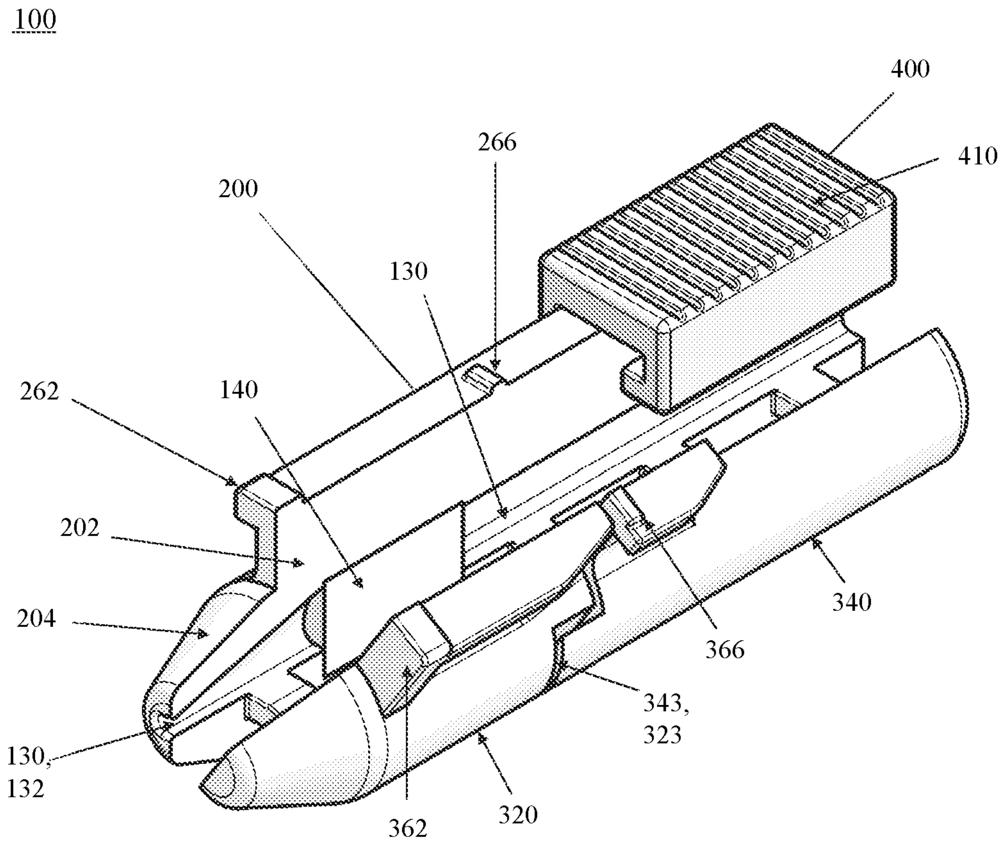
FIG. 6 shows a perspective view of the torque device in a first open state according to embodiments.
Figure 7:
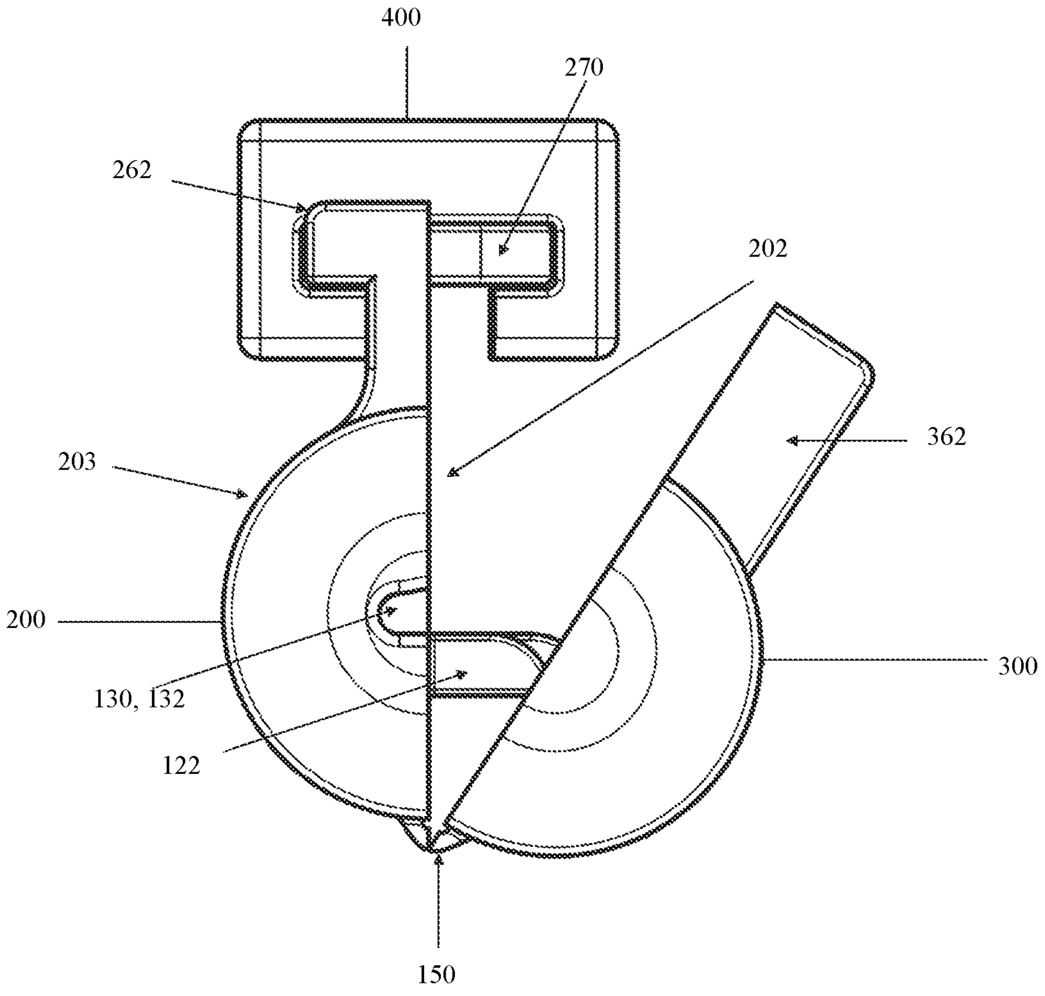
FIG. 7 shows a front view of the torque device shown in FIG. 6.
Figure 8:
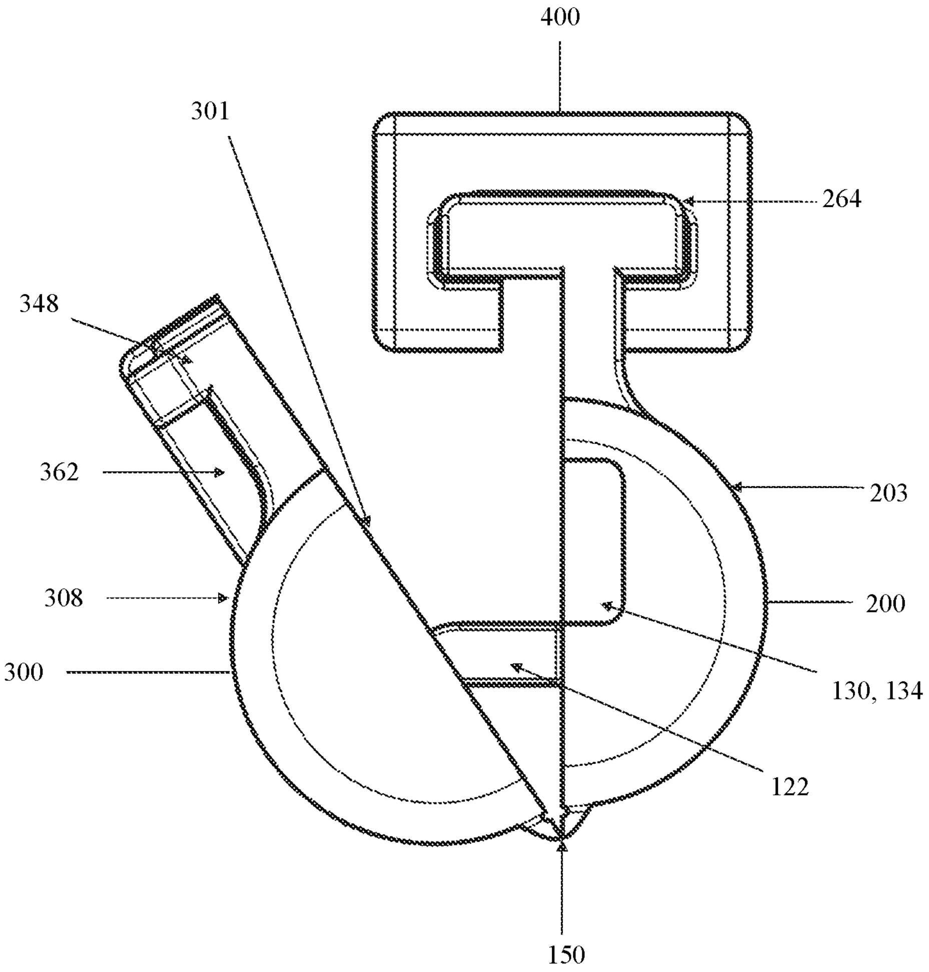
FIG. 8 shows a back view of the torque device shown in FIG. 6.
Figure 9:
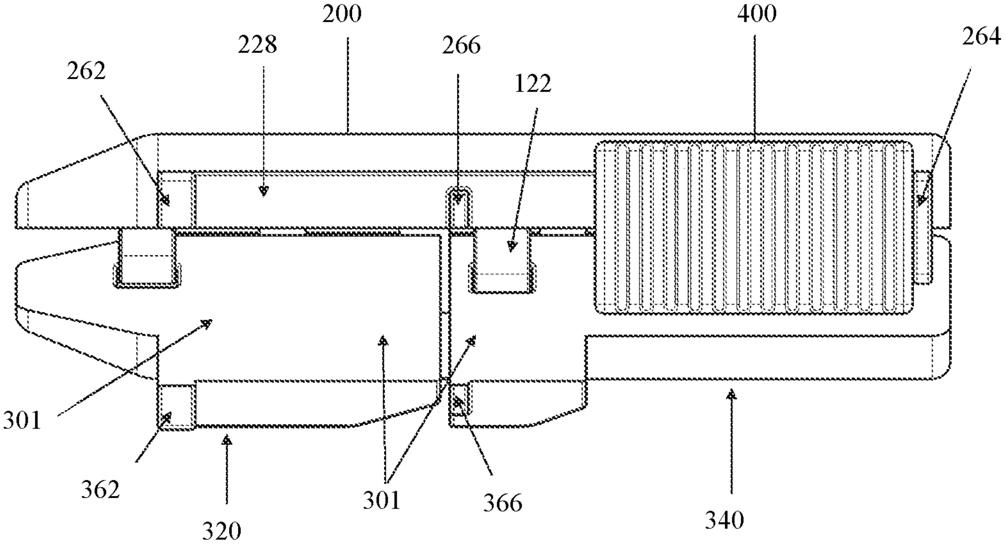
FIG. 9 shows a top view of the torque device shown in FIG. 6.
Figure 10:
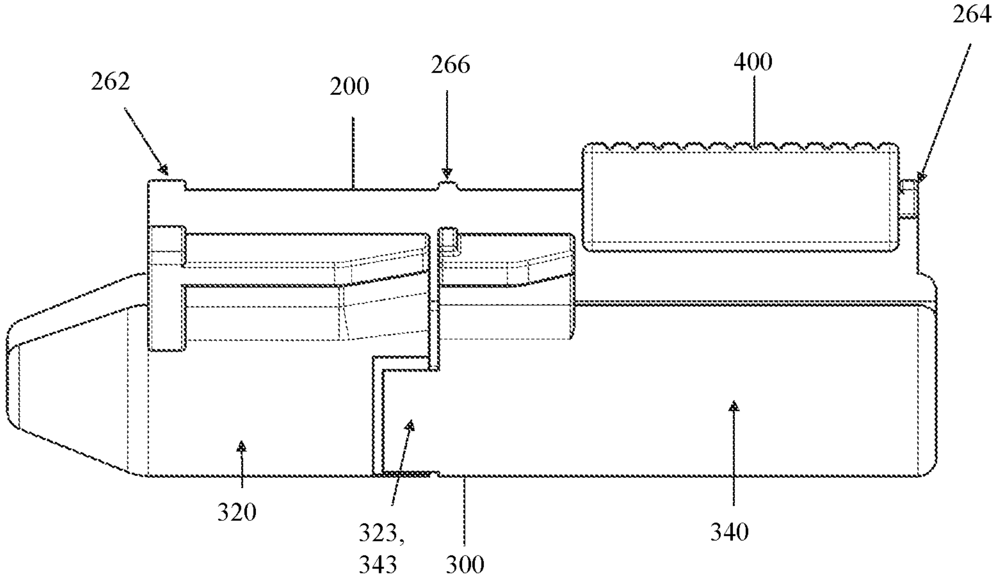
FIG. 10 shows a side view of the torque device shown in FIG. 6.
Figure 11:
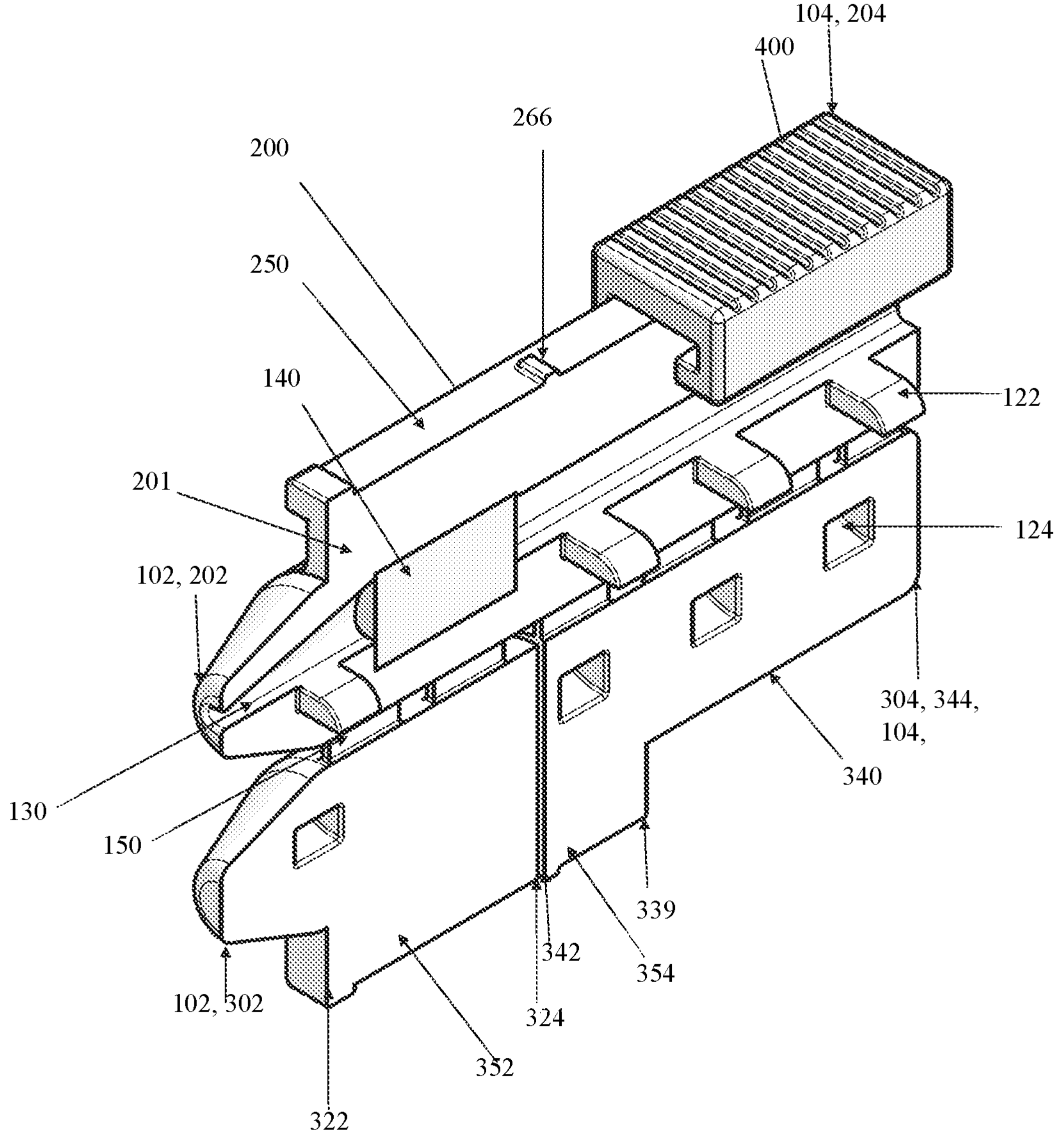
FIG. 11 shows another perspective view of the torque device in the first open state according to an embodiments.
Figure 12:
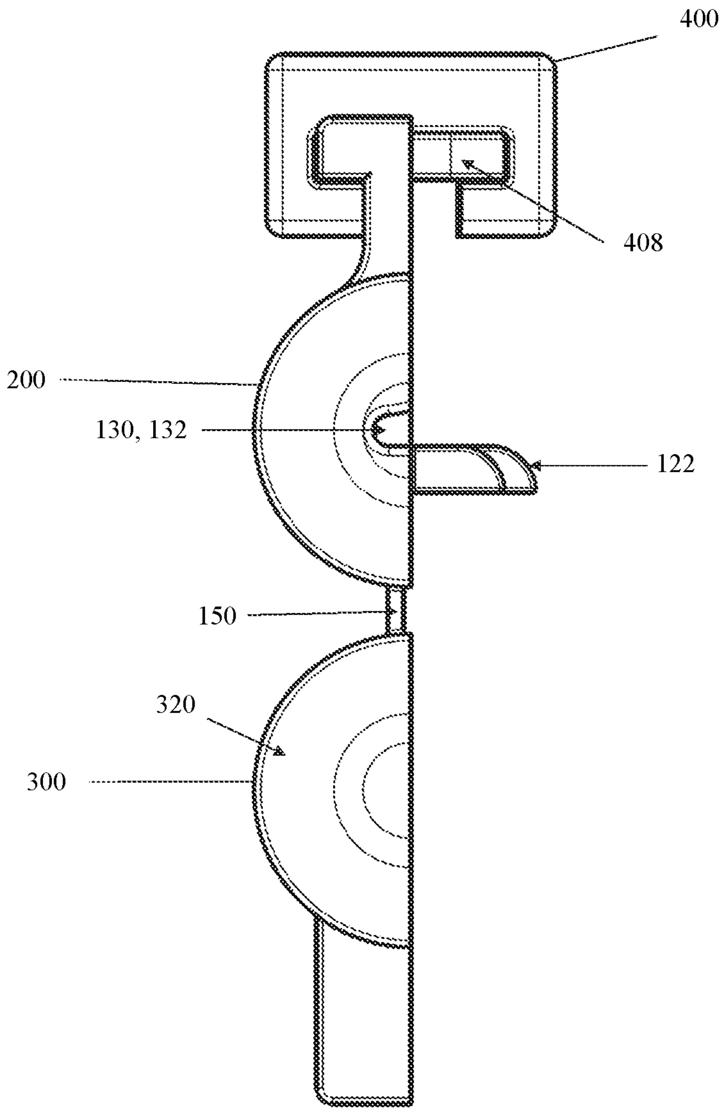
FIG. 12 shows a front view of the torque device shown in FIG. 11.
Figure 13:
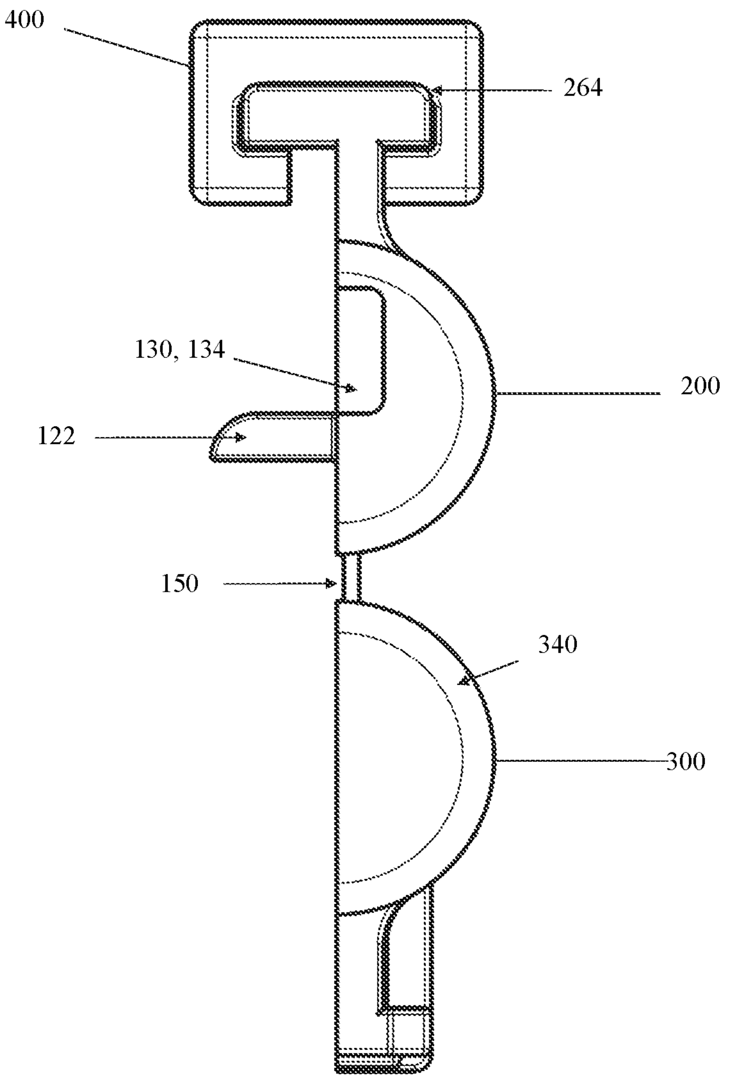
FIG. 13 shows a back view of the torque device shown in FIG. 11.
Figure 14:
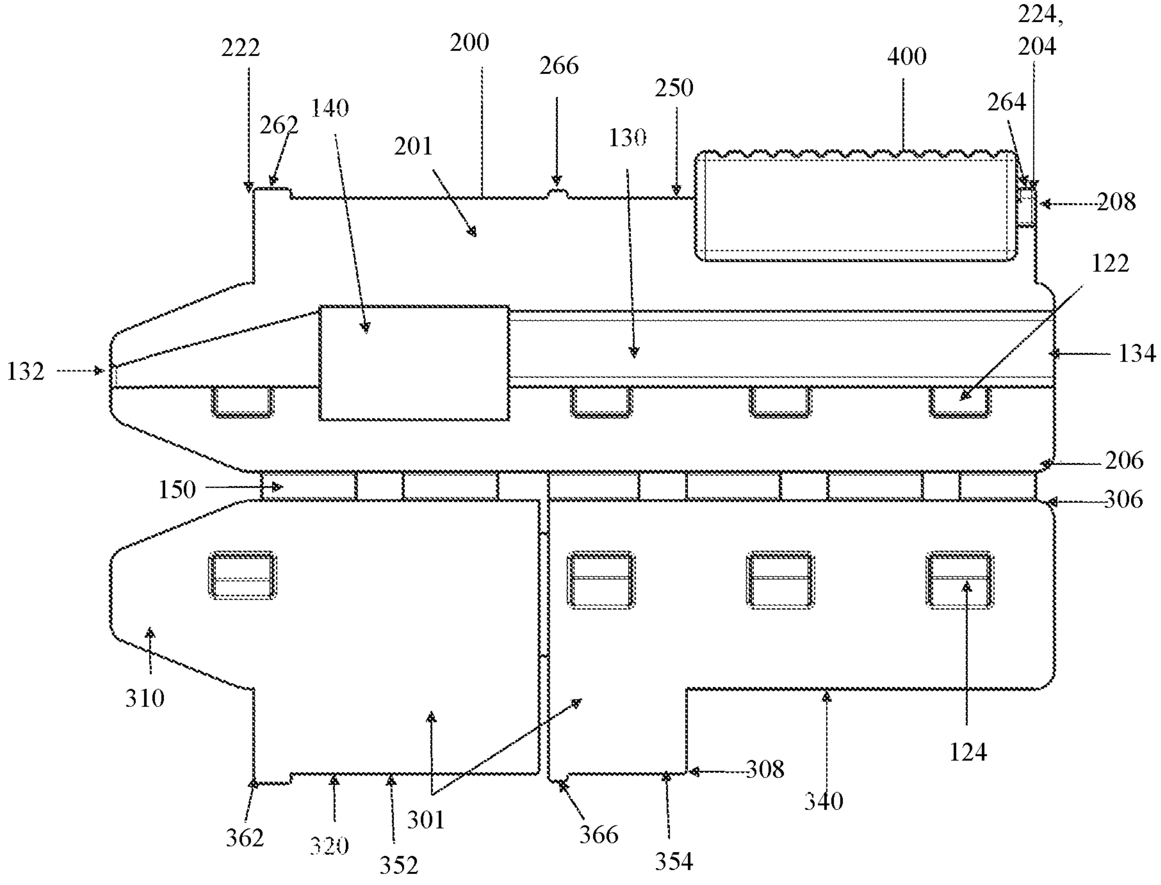
FIG. 14 shows a side view of the torque device shown in FIG. 11.
Figure 15:
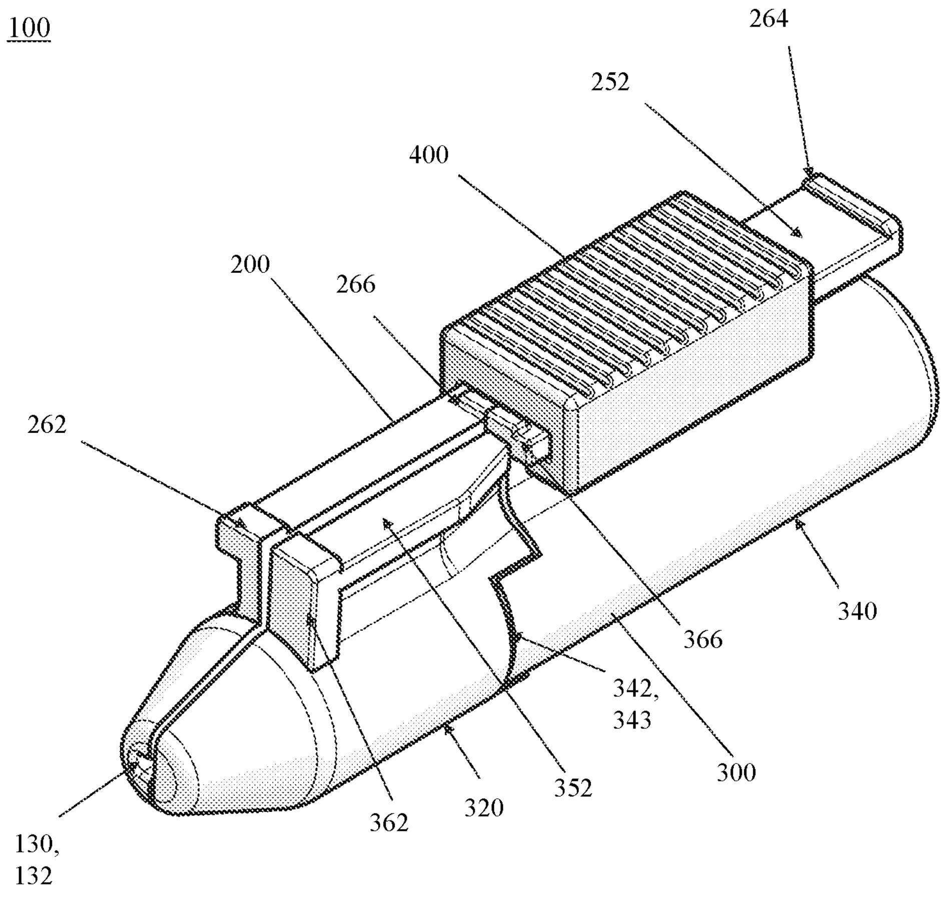
FIG. 15 shows a perspective view of the torque device in a second open state according to embodiments.
Figure 16:
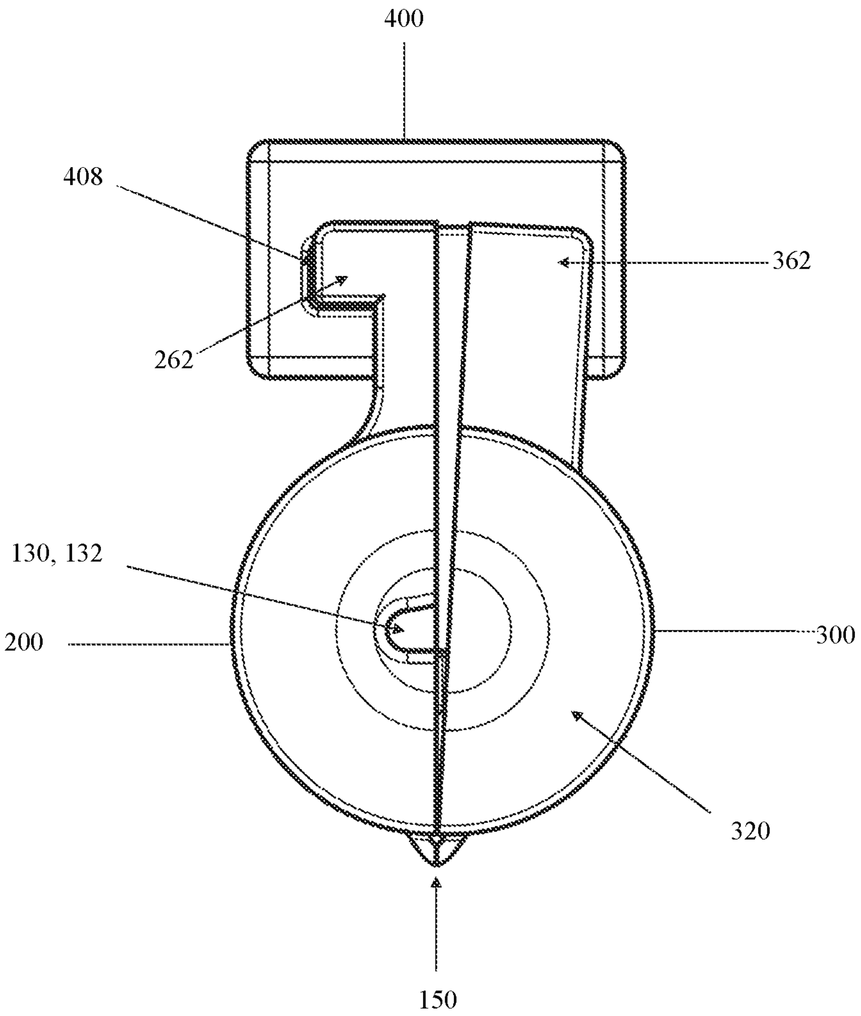
FIG. 16 shows a front view of the torque device shown in FIG. 15.
Figure 17:
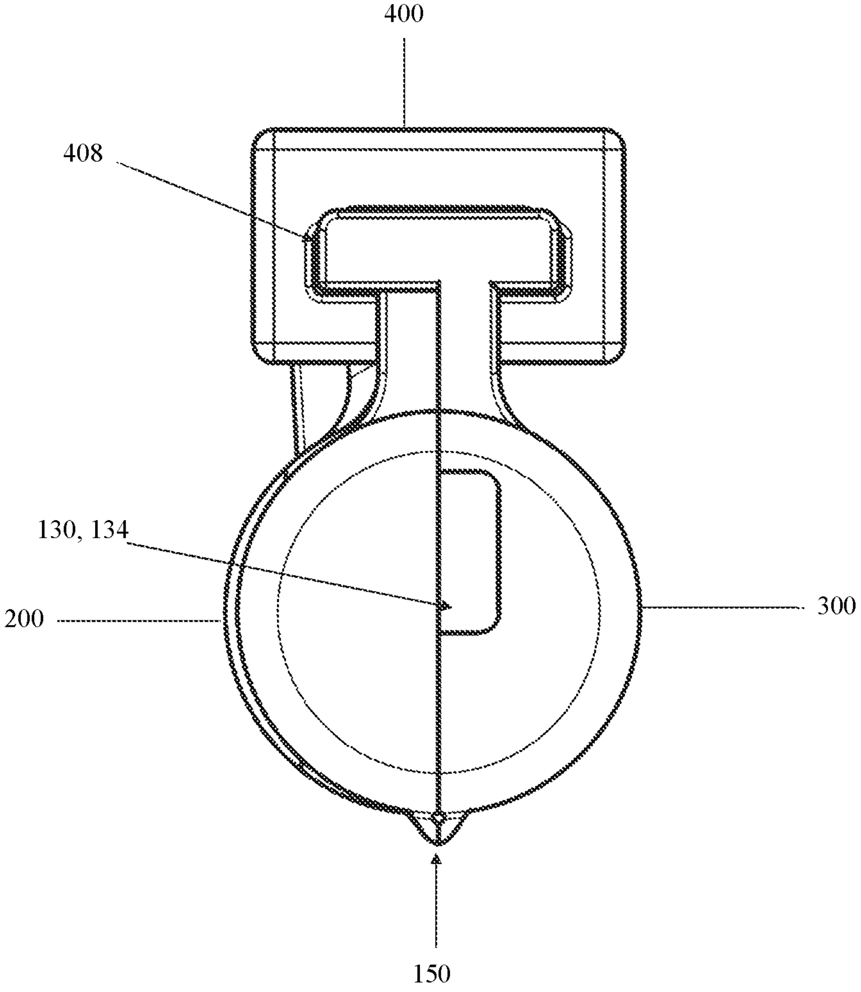
FIG. 17 shows a back view of the torque device shown in FIG. 15.
Figure 18:
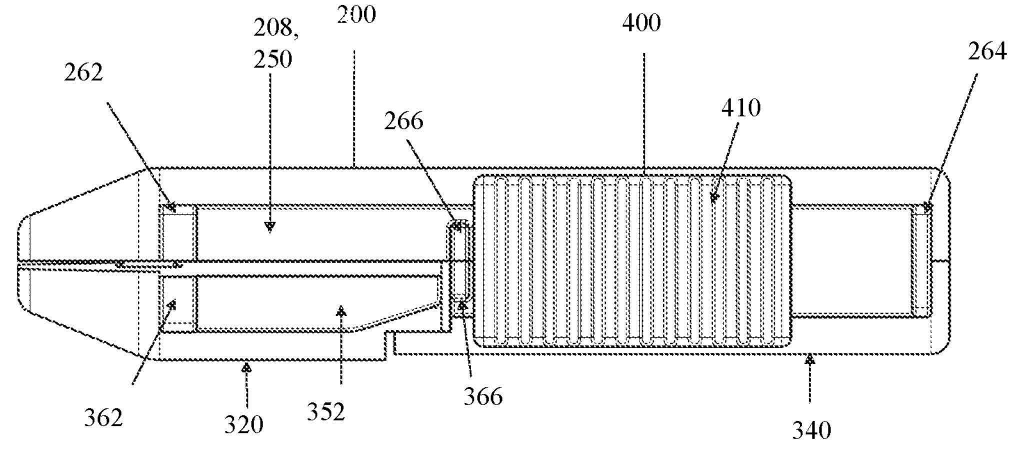
FIG. 18 shows a top view of the torque device shown in FIG. 15.
Figure 19:
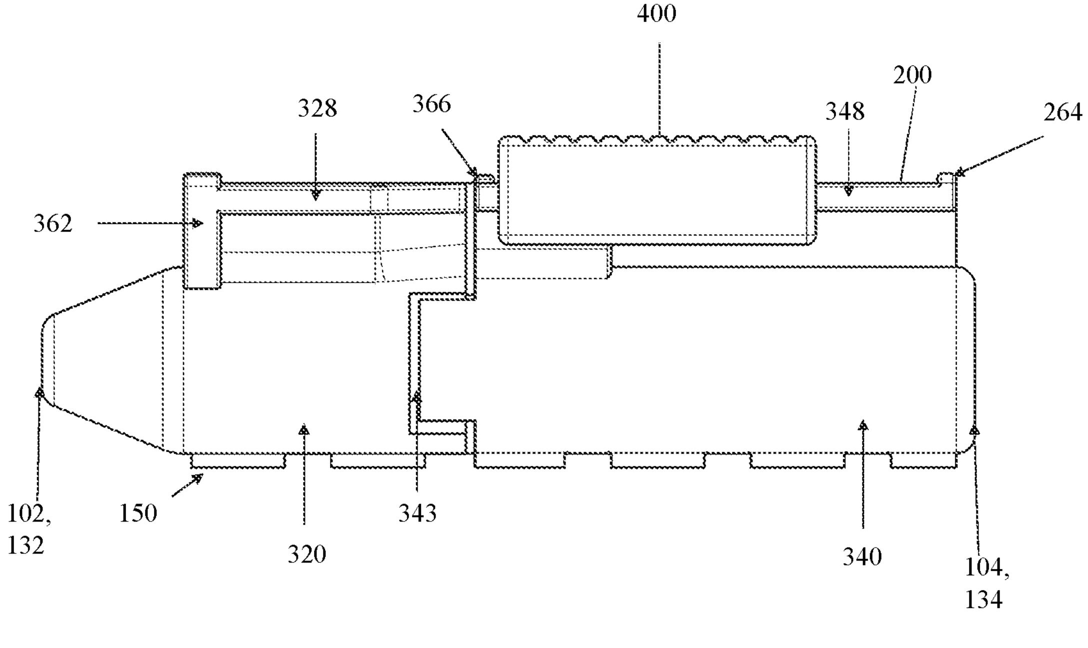
FIG. 19 shows a side view of the torque device shown in FIG. 15.

FIGS. 1-19 show views of a torque device 100 according to embodiments. The device 100 may include a first member 200, a second member 300, and a connecting member 150 that is disposed between and is coupled to a first side 202 of the first member 200 and a first side 302 the second member 300. The first member 200, the second member 300, and the connecting member 150 together can form the body of the device 100. The body of the device 100 may include a first end 102, a second end 104, and a length therebetween. In some embodiments, the device 100 may include an interior channel 150 disposed along the length. The device 100 may further include a locking member 400 configured to be slidably movable with respect to the length of the body. The locking member 400 may be coupled to the first member 200 and/or the second member 300.

The locking member 400 may be configured to cause the device 100 to be in one or more operation states based on the position of the locking member 400 with respect to the length of the body (the length of first member 200 and/or the second member 300). In some embodiments, the one or more operation states may include a closed state (also referred to as a "first state") and one or more open states. In some embodiments, the one or more open states may include a first open state (also referred to as a "second state") and a second open state (also referred to as a "third state").

FIGS. 1-5 show views of the torque device 100 in a closed (first) or locked state according to embodiments. FIGS. 6-19 show the torque device 100 in open states according to embodiments. For example, FIGS. 6-14 show the torque device 100 in a first open state and FIGS. 15-19 show the torque device 100 in a second open state according to embodiments. It will be understood that the torque device 100 may include more or less open states.

When the torque device 100 is on a guidewire in the closed or locked state as shown in FIGS. 1-5, the torque device 100 is clamped on the guidewire. In the closed state, the torque device can allow a user to use torque to move the guidewire (e.g., spin the wire around) through the torque device and a body of the patient. When the torque device 100 is in the first open state shown in FIGS. 6-14, the torque device can be loaded onto and/or removed from the guidewire (because it is completely unclamped from the guidewire). Additionally, for example, when the torque device 100 is in the first open state, as shown in FIGS. 11-14, a solution, such as a saline solution, may be used to coat and/or clean the interior of the torque device 100. When the torque device 100 is on a guidewire in the second (partially) opened state shown in FIGS. 15-19, the torque device is unclamped from the guidewire but still attached to the guidewire and thereby can allow advancement of the torque device over the guidewire while maintaining engagement of the guidewire and without affecting the position of the guidewire.

In some embodiments, the device 100 may include an opening 132 that communicates with the channel 130 at the first end 102 and an opening 134 that communicates with the channel 130 at the second end 104. In operation, when the device 100 is disposed on a guidewire, the first end 102 can be closest to the patient and the second end 104 is distal to the patient (i.e., closer to the clinician) on the guidewire.

In some embodiments, the first member 200 may include a first end 202 and a second end 204 and a length therebetween. The first end 202 may correspond to the first end 102 of the device and the second end 204 may correspond to the second end 104.

In some embodiments, the first member 200 may include a tip portion 210 and one or more body portions 220. In this example, the first member 200 may include (one) body portion 220. In some embodiments, as shown in the figures, the tip portion 210 and the body portion 220 may be adjacent to each other. In some embodiment, the tip portion 210 and the body portion 220 may be an integrated so that the tip portion 210 and the body portion 220 move together with respect to the connecting member 150. In some embodiments, the tip portion 210 may include the first end 202 and the body portion 220 may include the second end 204.

In some embodiments, the body portion 220 may have a first end 222, a second end 224, and a length therebetween. In some embodiments, the first member 200 may include an inner surface 201 and an outer surface 203. In some embodiments, the first member 220 may include a first side 206 and a second side 208. In some embodiments, the locking member 400 may be slidably coupled to at least a portion of the second side 208 and the connecting member 150 may be coupled to the first side 206.

In some embodiments, the second member 300 may include a first end 302 and a second end 304 and a length therebetween. The first end 302 may correspond to the first end 102 of the device and the second end 304 may correspond to the second end 104. In some embodiments, the first member 300 may include a tip portion 310 and one or more body portions. In this example, the first member 200 may include two body portions—a first body portion 320 and a second body portion 340. In some embodiments, as shown in the figures, the first body portion 320 may be disposed between the tip portion 310 and the second body portion 340.

In some embodiments, the tip portion 310 and the first body portion 320 may be adjacent to each other. In some embodiment, the tip portion 310 and the first body portion 320 may be an integrated so that the tip portion 310 and the body portion 320 move together; and the first body portion 320 (including the tip portion 310) and the second body portion 340 may be configured to move separately/independently with respect to the connecting member 150.

In some embodiments, the first body portion 320 may have a first end 322, a second end 324, and a length therebetween; and the second body portion 340 may have a first end 342 and a second end 344, and a length therebetween.

In some embodiments, the first body portion 320 may include a member 323 disposed at the second end 324 and the second body portion 340 may include a (complimentary)

member 343 disposed at the first end 342 configured to engage the first body portion 320 so that the second body portion 340 prevents the first body portion 320 from fully separating when only the second body portion 340 is engaged by the locking member 400. In some embodiments, the member 343 of the second body portion 300 may be a protrusion and the complementary member 323 of the first body portion 320 may be a recess on which the member 343 may be disposed so that the first body portion 320 and the second body portion 340 are flush when in the closed and/or partially open positions.

In some embodiments, the second member 300 may include an inner surface 301 and an outer surface 303. In some embodiments, the second member 300 may include a first side 306 and a second side 308. The locking member 150 may be slidably coupled to at least a portion of the second side 308 and the connecting member 150 may be coupled to the first side 306.

In some embodiments, the locking member 400 may include a first end 402, a second end 404, and a length therebetween. In some embodiments, the locking member 400 may include an inner surface 401 and an outer surface 403. In embodiments, the locking member 400 may include an inner channel 408 disposed on an inner surface 401 and configured to engage the second side of the body. In some embodiments, the locking member 400 may include one or more engaging members 410 disposed along its length on the outer or top surface 403. The one or more engaging members 410 may be configured to engage a finger of the user. The one or more engaging members 410 may include and is not limited to grooves, notches, protrusions, loops, among others, or any combination thereof. In some embodiments, the one or more engaging members 410 may be disposed in a pattern. For example, the one or more engaging members 410 may be spaced and disposed perpendicularly with respect to the length of the locking member 400.

In some embodiments, the device 100 may include one or more rails that form a slide track on which the locking member 400 may slidably move. The track may be complimentary to the inner channel 408 of the locking member 400. As shown in the figures, the track/rails may be disposed along the length of the body of the device 100.

In some embodiments, the one or more rails may be disposed along a portion of the length of the first member 200 along the second side 208 and/or the second member 300 along the second side 308. In this example, the first member 200 may include a rail 250 disposed along the entire length of the first member 200. In some embodiments, the width of the rail 250 may vary along the length. In some embodiments, the second member 300 may include a rail disposed along the first body portion 320 and/or the second body portion 340. In this example, the first body portion 320 may include a rail 352 disposed along its entire length and the second body portion 340 may include a rail 354 disposed along a portion of its length. In some embodiments, the width of the rail may vary along the length of the second member 300.

In some embodiments, the track may have a width. In some embodiments, the (largest) width of the rail 352 and the rail 354 may correspond to about a half of the width of the track. The portion of the rail 250 opposing the rail 352 and 354, for example, from the first end 222 to about a position 239 along its length may have a width that also corresponds to about a half of the width of the track. The portion of the rail 250 from the position 239 to the second end 224 may have a largest width that substantially corresponds to the width of the track.

In some embodiments, the device 100 may include one or more stopping members disposed along the track (i.e., (i) the rail 250 of the first member 200 and/or (ii) the rail 352 and/or the rail 354 of the second member 300). The one or more stopping members may be configured to (i) restrict the movement of the locking member 400 along the track to one or more specific positions and/or (ii) a tactile, audible and/or visual indication (e.g., sound, light, color, texture, etc.) associated with one or more specific positions along the track, to enable an operating state of the device 100 corresponding to the respective position.

In some embodiments, the first member 200 may include a first stopping member 262 a second stopping member 264, and a third stopping member 266; and the second member 300 may include a first stopping member 362 and a third stopping member 366. In some embodiments, the third stopping member 266, 366 may be disposed between the first stopping member 262, 362 and the second stopping member 264. In some embodiments, the first stopping member 262 and the first stopping member 362 may together form the first stopping member along the track; and the third stopping member 266 and the third stopping member 366 may together form the third stopping member along the track. In some embodiments, the first stopping member 262, 362 and the second stopping member 264 may be configured to stop the locking member 400 and the third stopping member 266, 366 may be configured to indicate a position along the track.

In some embodiments, the one or more stopping members may include a protrusion. In some embodiments, the third stopping member 266, 366 may be different from the first stopping member(s) 262, 362 and/or the second stopping member(s) 264. For example, the third stopping member 266, 366 may have a different size (e.g., height/width), color, texture, shape, among others, or any combination thereof as compared to the first stopping member and/or the second stopping member. As shown in the figures, the third stopping member 266, 366 may have a different size than the first stopping member 262, 362 and the second stopping member 264.

In some embodiments, the device 100 may include different additional and/or alternative stopping members, rails and/or track. For example, the device 100 may include more or less stopping members, more or less tracks, different sized and/or shaped stopping members, different sized and/or shaped tracks, among others, or a combination thereof. In some embodiments, the one or more stopping members may include the same and/or different tactile, audible and/or visual indications.

In some embodiments, the connecting member 150 may be a hinge. In some embodiments, the hinge may include but is not limited to a living hinge. In some embodiments, the connecting member 150 may be composed of a different material than one or more members of the body and/or separately attached to the one or more members.

In some embodiments, the interior channel 130 may be formed by a recess disposed along the length of the device 100. The recess may be disposed within the first member 200 and/or the second member 300. In some embodiments, the internal channel 130 may be a recess disposed along the length of the first member 200 as shown in the figures. The size of the recess may correspond to the size of the guidewire. For example, the interior channel may be sized to accommodate any guidewire size (e.g., 014 mm-0.038 mm) when the body 100 is in the closed state. In some embodiments, the opening 132 and the opening 134 may be disposed in the first member 200.

In some embodiments, the device 100 may include one or more of guiding members disposed on the first member 200 and/or the second member 300 bordering the interior channel 130. The one or more guiding members may be configured to guide the guidewire into the interior channel 130.

In some embodiments, the one or more guiding members may include one or more protruding members 122 disposed on one of the first member 200; and one or more receiving members 124 disposed on the second member 300 complimentary to the one or more protruding members and configured to receive the one or more protruding members 122. As shown in the figures, the one or more receiving members 124 may be recesses or openings disposed at positions along the second member 300 corresponding to position and shape of the protruding members 122. As shown in the figures, the first body portion 220 and the first body portion 320 may include at least one set of guiding members disposed between the tip portion 210, 310 and the first stopping member 262, 362, respectively; and the first body portion 220 and the second body portion 340 may include at least three sets disposed between the second stopping member 266 and the third stopping member 266, 366. The device 100 may include more or less sets of guiding members.

In some embodiments, the device 100 may include a clamping pad 140 disposed along the interior channel 130. In some embodiments, the clamping pad 140 may be disposed on the first body portion 220 to correspond to the first body portion 320 of the second member 300. When the device 100 is in the closed state as shown in FIGS. 1-5, the clamping pad 140 may be configured to apply pressure to a guidewire disposed within the interior channel 130 thereby preventing movement of the device 100 with respect to the guidewire. For example, the pressure asserted by the first body portion 320 when in the closed position causes the clamping pad 140 to hold the guidewire in place requiring a user to torque the guidewire to move the guidewire with respect to the device 100. In some embodiments, the clamping pad 140 may be made of any material capable of causing friction with respect to the guidewire. For example, the materials may include but is not limited to rubber.

In use, a user can move the locking member 400 on the track to different positions along the track with respect to the stopping members and/or portions of the first member 200 and/or the second member 300 for different operation states of the device.

For example, when a user slides the locking member 400 along the track to engage the first stopping member (stopping members 262 and 362) at a first position shown in FIGS. 1-5, the locking member 400 causes the first member 200 and the second member 300 to mate thereby closing the device 100. As shown in FIG. 1-5, the locking member 150 can be at the first position when it is disposed between the first stopping member 262, 362 and the third stopping member 266, 366 so that the first member 200 mates with the second member 300. In the first position/closed state, the locking member 150 can engage the rail 352 of the first body portion 320 and the rail 354 of the second body portion 340 of the second member 300 and corresponding portions of the rail 250 of the first body portion 220. This engagement can cause the guiding members (also referred to as "one or more protruding members") 122 of the first body portion 210 of the first member 200 to mate with the corresponding guiding members (also referred to as "one or more receiving members") 124 of the first body portion 320 and the second body portion 340 of the second member 300, thereby causing the clamping pad 140 to assert friction/pressure onto a guidewire disposed in the channel 130. This can cause the torque device 100 to be clamped onto the guidewire, thereby can prevent movement of the torque device 100 with respect to the guidewire. In the first position/closed state, the device 100 can require a user to use torque to move/spin the guidewire with respect to the torque device 100.

To cause the device 100 to be in one or more open states, a user can slide the locking member 400 towards the second stopping member 264 so that the locking member 400 is disposed at one or more positions between the second stopping member 264 and the third stopping members 266, 366. For a partially open state or second open state as shown in FIGS. 15-19, the locking member 400 can be moved so that it is disposed at a third position that is (i) between the second stopping member 264 and the third stopping member 266, 366 and (ii) abuts the third stopping member 266, 366. In the third position/second open state, the first body portion 320 of the second member 300 may not be completely mated with the first member 200, thereby removing pressure from the clamping pad 140. The protrusion 343 of the second body portion 340 may be configured to prevent the first body portion 320 to fully open via the recess 323. This allows the torque device to be attached to the guidewire while advancement, thereby preventing unwanted removal.

For a fully open state or first open state in which the device 100 may be loaded onto and/or removed from a guidewire as shown in FIGS. 6-14, the locking member 400 can be moved so that it is disposed at a second position that is (i) between the second stopping member 264 and the third stopping members 266, 366 and (ii) abuts the second stopping member 264. In the second position/first open state, the locking member 400 may be configured to disengage the rails 352, 354 of the second member 300, thereby enabling the second member 300 to separate from the first member 200.

The device 100 may be moved between these positions using only one finger of the user. Thereby, the rest of the hand of the user can be available to control the guidewire. This eliminates the need for another user in the operation of this torque device. The device according to the disclosure can therefore provide better control of the guidewire while reducing opportunities for user-error resulting in better outcomes for both the clinician and patient.

The device is not limited to the configuration, shape, size, etc. shown in the figures and described above. For example, the first member, the second member, the locking member, and/or the connecting member may have a different configuration, size (bigger and/or smaller length, height/width, etc.), shape, among others, or any combination thereof. By way of example, the first member 200 may include more than one body portion 220; the tip portion 210 and the body portion 220 may be separately/independently movable; among others; or a combination thereof. By way of another example, the second member 300 may include more or less body portions; among others; or a combination thereof.

In some embodiments, the torque device may be sterilized. In further embodiments, the torque device may be a single-use device. In further embodiments, the torque device may be disposable. In some embodiments, the torque device may be preloaded with a guidewire.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A torque device comprising:

a body including a first end, a second end, and a length therebetween, the body including:

a first member, a second member, and a connecting member that couples the first member and the second member, the first member and the second member being configured to move with respect to the connecting member so that the first member and the second member face each other;

an interior channel disposed along the length and configured to receive a guidewire; and each of the first member and the second member including a first side and a second side, each side being parallel to the length of the body, the connecting member being disposed on the first side of the first member and the second member; and a locking member slidably coupled to the first member and/or the second member, the locking member being configured to move along at least a portion of the second side of the first member and the second member between one or more positions corresponding to one or more operation states, the one or more operation states including a closed state in which the second side of the first member and the second side of the second member are fixedly secured with respect to the locking member, and one or more open states in which at least a portion of the second side of first member and at least a portion of the second side of the second member are separated;

wherein:

the body includes one or more guiding members disposed on the first member and/or the second member bordering the interior channel; and the one or more guiding members is configured to guide the guidewire into the interior channel.

2. The torque device of claim 1, wherein:

the one or more guiding members includes one or more protruding members disposed on one of the first member or the second member and one or more receiving members complimentary to the one or more protruding members, the one or more receiving members being configured to receive the one or more protruding members and being disposed on the other of the first member or the second member.

3. The torque device of claim 1, wherein:

the body includes a track disposed on the second side and on which the locking member is configured to move;

the first member includes a first body portion, and the second member includes a first body portion and a second body portion; and each of (i) the first body portion of the first member and/or (ii) the first body portion and/or the second body portion of the second member includes a rail disposed at least along partially the length thereof that forms the track.

4. The torque device of claim 1, wherein:

each of the first member and the second member includes a tip portion and one or more body portions.

5. The torque device of claim 1, wherein:

the first member includes a tip portion and a body portion; and the second member includes a tip portion, a first body portion and a second body portion, the first body portion being between the tip portion of the second member and the second body portion.

6. The torque device of claim 5, wherein:

the first member and/or the second member includes the interior channel; and the body includes a clamping member disposed along the interior channel of the first member and/or the second member, the clamping member being configured to clamp on the guidewire when disposed within the interior channel and the body is in the closed state.

7. The torque device of claim 6, wherein the clamping member is disposed along the body portion of the first member to oppose the first body portion of the second member.

8. The torque device of claim 1, wherein the connecting member is a hinge.

9. The torque device of claim 1, wherein the connecting member is a living hinge.

10. The torque device of claim 1, wherein the locking member includes one or more engaging members disposed on a surface.

11. The torque device of claim 10, wherein the one or more engaging members includes one or more protrusions and/or depressions.

12. A torque device, comprising:

a body including a first end, a second end, and a length therebetween, the body including:

a first member, a second member, and a connecting member that couples the first member and the second member, the first member and the second member being configured to move with respect to the connecting member so that the first member and the second member face each other;

an interior channel disposed along the length and configured to receive a guidewire; and each of the first member and the second member including a first side and a second side, each side being parallel to the length of the body, the connecting member being disposed on the first side of the first member and the second member; and a locking member slidably coupled to the first member and/or the second member, the locking member being configured to move along at least a portion of the second side of the first member and the second member between one or more positions corresponding to one or more operation states, the one or more operation states including a closed state in which the second side of the first member and the second side of the second member are fixedly secured with respect to the locking member, and one or more open states in which at least a portion of the second side of first member and at least a portion of the second side of the second member are separated;

wherein:

the first member includes a tip portion and a body portion;

the second member includes a tip portion, a first body portion and a second body portion, the first body portion being between the tip portion of the second member and the second body portion;

the one or more positions includes a first position, a second position and a third position, the third position being disposed along the length of the body between the first position and the second position; the first position corresponds to the closed state;

the one or more open states includes a first open state and a second open state; the second position corresponds to the first open state is in which (i) the first body portion of the second member and the body portion of the first member are separated along the second side and (ii) the second body portion of the second member and the body portion of the first member are separated along the second side; the third position corresponds to the second open state in which (1) the first body portion of the second member and the body portion of the first member are separated along the second side and (ii) the second body portion of the second member and the body portion of the first member abut each other; and the first body portion of the second member and the second body portion of the second member are separately moveable in (i) the first open state when the locking member is in the second position and/or (ii) the second open state when the locking member is in the third position.

13. The torque device of claim 12, wherein:

the tip portion and the body portion of the first member are integrated; and the tip portion and the first body portion of the second member are integrated.

14. A torque device, comprising:

a body including a first end, a second end, and a length therebetween, the body including:

a first member, a second member, and a connecting member that couples the first member and the second member, the first member and the second member being configured to move with respect to the connecting member so that the first member and the second member face each other;

an interior channel disposed along the length and configured to receive a guidewire; and each of the first member and the second member including a first side and a second side, each side being parallel to the length of the body, the connecting member being disposed on the first side of the first member and the second member; and a locking member slidably coupled to the first member and/or the second member, the locking member being configured to move along at least a portion of the second side of the first member and the second member between one or more positions corresponding to one or more operation states, the one or more operation states including a closed state in which the second side of the first member and the second side of the second member are fixedly secured with respect to the locking member, and one or more open states in which at least a portion of the second side of first member and at least a portion of the second side of the second member are separated;

wherein:

the one or more positions includes a first position and a second position;

the body includes a plurality of stopping members disposed along the second side of the first member and/or the second member;

the plurality of stopping members includes a first stopping member and a second stopping member;

the locking member is configured to slidably move between the first stopping member and the second stopping member;

the first position corresponds to when the locking member is adjacent to the first stopping member; and the second position corresponds to when the locking member is adjacent to the second stopping member.

15. The torque device of claim 14, wherein the plurality of stopping members are disposed on the second side of the first member and/or the second member.

16. The torque device of claim 14, wherein:

the one or more positions further includes a third position, the third position being disposed along the length of the body between the first position and the second position the plurality of stopping members includes a third stopping member disposed between the first stopping member and the second stopping member; and the first position corresponds to when the locking member is disposed between the first stopping member and the third stopping member;

the second position corresponds to when the locking member is disposed between the second stopping member and the third stopping member and the locking member abuts the second stopping member; and the third position corresponds to when the locking member is disposed between (i) the second stopping member and the third stopping member and (ii) the locking member abuts the third stopping member.

17. The torque device of claim 16, wherein the first stopping member is disposed on the first member and the second member, and the third stopping member is disposed on the first member and the second member.

18. The torque device of claim 17, wherein the second stopping member is disposed on the first member.

* * * * *